(12) United States Patent
Lacroix et al.

(10) Patent No.: US 8,183,534 B2
(45) Date of Patent: May 22, 2012

(54) SCINTILLATING FIBER DOSIMETER ARRAY

(76) Inventors: Frederic Lacroix, Montreal (CA); Luc Beaulieu, Quebec (CA); Sam Beddar, Houston, TX (US); Mathieu Guillot, Quebec (CA); Luc Gingras, Quebec (CA); Louis Archambault, Houston, TX (US)

( * ) Notice: Subject to any disclaimer, the term of this patent is extended or adjusted under 35 U.S.C. 154(b) by 0 days.

(21) Appl. No.: 12/276,013

(22) Filed: Nov. 21, 2008

(65) Prior Publication Data

US 2009/0236510 A1    Sep. 24, 2009

Related U.S. Application Data

(60) Provisional application No. 60/989,637, filed on Nov. 21, 2007.

(51) Int. Cl.
*G01T 1/02* (2006.01)
*G01T 1/24* (2006.01)
*G01T 1/26* (2006.01)

(52) U.S. Cl. ............... 250/370.07; 250/370.09; 250/371

(58) Field of Classification Search ............... 250/252.1, 250/370.07, 370.11, 371, 370.09; 385/12
See application file for complete search history.

(56) References Cited

U.S. PATENT DOCUMENTS

| | | | |
|---|---|---|---|
| 5,265,475 A * | 11/1993 | Messinger et al. | 73/800 |
| 5,856,673 A * | 1/1999 | Ikegami et al. | 250/368 |
| 5,905,263 A | 5/1999 | Nishizawa et al. | |
| 6,066,851 A * | 5/2000 | Madono et al. | 250/367 |
| 6,087,666 A * | 7/2000 | Huston et al. | 250/484.5 |
| 6,125,335 A | 9/2000 | Simon et al. | |
| 7,154,097 B2 | 12/2006 | Fontbonne et al. | |
| 7,432,510 B2 * | 10/2008 | Yeo | 250/374 |
| 7,804,075 B2 * | 9/2010 | Ntziachristos et al. | 250/458.1 |
| 2006/0017009 A1 * | 1/2006 | Rink et al. | 250/484.5 |
| 2006/0027756 A1 * | 2/2006 | Thomson et al. | 250/370.07 |
| 2009/0014665 A1 * | 1/2009 | Fleming et al. | 250/484.5 |

OTHER PUBLICATIONS

Fontbonne, Jean-Marc, Conception et réalisation d'un dosimètre à scintillation adaptéà la dosimétrie de faisceaux de rayonnements ionisants en radiothérapie, Thèse en vue de l'obtention du Doctorat de l'Université de CAEN, Dec. 1992, pp. 1-174.

Fontbonne et al., Scintillating fiber dosimeter for radiation therapy accelerator, IEEE transactions on nuclear science, vol. 49, No. 5, Oct. 2002, pp. 2223-2227.

Frelin et al., Spectral discrimination of Cerenkov radiation in scintillating dosimeters, Am. Assoc. Phys. Med., Sep. 2005, pp. 3000-3006.

Almond et al., AAPM's TG-51 protocol for clinical reference dosimetry of high-energy photon and electron beams, Am. Assoc. Phys. Med., Sep. 1999, pp. 1847-1870.

* cited by examiner

*Primary Examiner* — David Porta
*Assistant Examiner* — Faye Boosalis
(74) *Attorney, Agent, or Firm* — Bereskin & Parr LLP

(57) ABSTRACT

A radiation dosimetry apparatus and method use a scintillating optical fiber array for detecting dose levels. The scintillating optical fiber detectors generate optical energy in response to a predetermined type of radiation, and are coupled to collection optical fibers that transmit the optical energy to a photo-detector for conversion to an electrical signal. The detectors may be embedded in one or more modular, water-equivalent phantom slabs. A repeatable connector couples the collection fibers to the photo-detector, maintaining the fiber ends in a predetermined spatial relationship. The detector fibers may be distributed as desired in a three-dimensional detection space, and may be oriented with their longitudinal axes at different orientations relative to a transmission axis of an incident radiation beam. A calibration method uses two measurements in two spectral windows, one with irradiation of the scintillator at a known dose and one with only irradiation of the collection fiber.

21 Claims, 9 Drawing Sheets

FIGURE 3A  FIGURE 3B

SCINTILLATING FIBER DOSIMETER ARRAY

FIELD OF THE INVENTION

This invention relates generally to the field of dosimetry and, more particularly, to rapid, high-resolution dosimeters for advanced treatment technologies.

BACKGROUND OF THE INVENTION

Treatment modalities such as Intensity Modulated Radiotherapy (IMRT), helical tomotherapy and radiosurgery are pushing current dosimeter technologies to their limits. Two major driving forces are involved: 1) complex, two-dimensional field patterns encountered in IMRT and tomotherapy require high resolution (i.e., small volume) dosimeters that can be stacked or arrayed to provide a rapid but precise two- or three-dimensional dose measurement, which in turn requires that the dosimeters be water-equivalent in order not to disturb the fluence in the measurement plane and 2) small fields used in all three treatment modalities, down to $1 \times 1$ cm$^2$ in IMRT and just a few millimeters in radiosurgery, give rise to volume effects such as spatial averaging in most dose detectors with detecting volumes larger than a few cubic millimeters.

Radiographic films possess high spatial resolution and are used for two-dimensional dose measurements. They are, however, subject to drawbacks. The need to develop the films before reading makes their use for online assessment impossible. Moreover, the development process affects the film response. Radiographic films are also notorious for over-responding to low-energy photons and they are not water-equivalent. Finally, the precision of a radiographic film used for dose measurement in the clinic is often limited to ±5%. Radiochromic films, which do not require development and are closer to water-equivalence in the megavoltage energy range, can also be used to evaluate dose distributions. However, radiochromic films are temperature dependent and sensitive to ultraviolet light. Achieving better than 5% reproducibility in routine fashion with radiochromic film is also challenging.

Detector arrays have been implemented in the clinic to achieve a faster and more precise dose reading than films. To date these arrays have been made of either semiconductor dose detectors or ion chambers. These arrays allow online evaluation of a dose pattern with the precision of a single dosimeter. The spacing between the detectors determines the resolution of an array: the closer the detectors are to each other, the more continuous the dose information will be. Because the materials used with current detector arrays are not water-equivalent (typically made of silicon or air), the use of such an array creates a perturbation in the particle fluence. Moreover, the non-water equivalence of these detectors prevents the use of three-dimensional arrays with closely packed detectors. The current detector arrays also suffer from other limitations depending on the type of detector in use. For semiconductor detectors, there may be significant angular dependence and poor reproducibility for low dose fractions. For ion chambers there may be some dose averaging because their detecting volume is usually larger than other dose detectors. Thermoluminescent detectors (TLD) have also been used in groups to measure dose at different location simultaneously, but the need to read each one individually limits frequent use of a large number of TLDs.

All of the above-mentioned detectors allow, at most, measurements in two-dimensional planes. The only detectors that can be used for three-dimensional measurements are dosimetric gels. Dosimetric gels are either based on the behavior of ferrous ions or on the polymerization of a monomer. They can be produced using a large variety of chemical formulas and each has its own set of advantages and disadvantages. However, most gels share a delicate fabrication process and require a time-consuming development process that makes them unsuitable for online measurements.

One of the key properties that is desired in the next-generation dosimetry systems is water-equivalence. Water-equivalence guarantees that the measurement instrument, when immersed in a water tank, does not perturb the beam fluence and allows stacking and arraying of multiple dosimeters in the treatment field for two- or three-dimensional dose measurements. In order to facilitate the quality assurance of complex treatment modalities, there exists a need for small, water-equivalent dosimeters.

SUMMARY OF THE INVENTION

In accordance with the present invention, a radiation dosimeter is provided for measuring a relative dose of a predetermined radiation type within a detection region by using a plurality of scintillating optical fibers. The scintillating optical fibers are located in a predetermined spatial arrangement in the detection region, and generate optical energy in response to irradiation with the predetermined radiation type. Optically coupled to the scintillation optical fibers are a plurality of collection optical fibers that receive the optical energy generated by the scintillation optical fibers. The collection optical fibers transmit the optical energy to a photo-detector that, in turn, generates electrical signals indicative of the optical energy received.

In an exemplary embodiment, a phantom material, such as a water-equivalent material, is located within the detection space, and the scintillation optical fibers are embedded in the phantom material. The phantom material may take the form of a plurality of modular slabs, at least some of which have the scintillation optical fibers embedded within. Slabs with no scintillation optical fibers may also be used as desired for equilibrium material.

The scintillation optical fibers are relatively short in length, and function as small local radiation detectors. These detectors may be distributed as desired within a three-dimensional detection space so as to gather data regarding dose distribution within the space. The scintillation optical fibers may be arranged parallel to each other or perpendicular, or in any other desired arrangement. In one embodiment, a longitudinal axis of the scintillation optical fibers is perpendicular to a transmission axis of a radiation beam being used while, in another, the longitudinal axis is parallel to the beam axis. Similarly, a plurality of the scintillating fibers may all reside in a common plane perpendicular to the beam axis, or there may be scintillating fibers located in multiple such planes.

The photo-detector of the present invention has an imager that converts the optical energy transmitted by the collection optical fibers to an electric signal that may thereafter be converted to a dose. It may also include a set of optical filters that allow discrimination between the light produced through scintillation and light produced through other means. In an exemplary embodiment, a housing surrounds the photo-detector components and shields them from stray light and radiation.

An optical connector may also be used for providing repeatable optical coupling between the collection optical fibers and the photo-detector. The photo-detector imager takes a two-dimensional image of the input optical signals. The connector may be such that it maintains the output ends of the collection optical fibers in a predetermined spatial relationship relative to one another, and connects to the photo-detector in such a way that the collection optical fibers have a precise location relative to the imager. In one embodiment, the connector maintains the collection optical fibers in an equally-spaced arrangement that minimizes optical crosstalk between the optical signals that are output from the fibers. Various arrangements of the collection optical fibers relative to the imager may be used, such that a correlation between the image taken by the photo-detector and the spatial distribution of the scintillating optical fiber detectors may be selected as desired by the user.

Also provided with the present invention is a method of calibrating a radiation dosimeter that uses a scintillating optical fiber that generates optical energy in response to irradiation with a predetermined radiation type and that is coupled to a collection optical fiber. The dose measured by such a dosimeter may be characterized as being proportional to a linear combination of a first dosimeter gain coefficient times a magnitude of optical energy collected by the collection optical fiber in a first spectral window plus a second dosimeter gain coefficient times the optical energy collected by the collection optical fiber in a second spectral window. The first spectral window may then be selected as matching an emission spectrum of the scintillating optical fiber, and the second spectral window as being substantially outside of the first spectral window.

In performing the calibration, a portion of the collection optical fiber is irradiated with the predetermined radiation type while irradiation of the scintillating optical fiber is avoided or minimized. During this irradiation, a first measurement is made of the magnitude of optical energy in the collection optical fiber for each of the first spectral window and the second spectral window. The scintillating optical fiber is then irradiated with a known dose of the predetermined radiation type and a second measurement is made of the magnitude of the optical energy in the collection optical fiber for each of the first spectral window and the second spectral window. From the first measurement, a non-scintillation optical energy ratio can be determined. This is the ratio between the magnitude of the optical energy in the first spectral window found during the first measurement and the magnitude of the optical energy in the second spectral window found during the first measurement. The first dosimeter gain coefficient may then be determined by dividing the known dose by a value equal to the magnitude of the optical energy measured in the first spectral window during the second measurement minus a multiplication product of the non-scintillation optical energy ratio and the magnitude of the optical energy measured in the second spectral window during the second measurement.

The calibration method allows proper determination of a gain coefficient for the dosimeter despite the presence of parasitic radiation such as Čerenkov light resulting from irradiation of the collection fiber with the predetermined radiation type. Such non-scintillation radiation is generated in the entire spectral range but with different yield in each spectral window. The method may also be applied to a radiation dosimeter having multiple pairs of scintillating optical fibers and accompanying collection optical fibers and, when the scintillating/collection fiber pairs are similar construction, calibration of one may be applied to the others. That is, the calibration values determined during calibration of one of the scintillating/collection optical fiber pairs may be applied to each of the other scintillating/collection optical fiber pairs of the dosimeter. Moreover, the calibration method may be conducted with only one predetermined dose measurement.

BRIEF DESCRIPTION OF THE DRAWINGS

FIG. 3A is a schematic view of a layout of scintillating fiber detectors embedded in a water-equivalent slab, where the fiber detectors are parallel and aligned at a mid-line of the slab.

FIG. 3B is a schematic view of an alternative layout of scintillating fiber detectors embedded in a water-equivalent slab, where the fiber detectors are distributed in an "X" pattern.

DETAILED DESCRIPTION

The present invention provides a dosimeter that makes use of scintillating optical fiber detectors. In an exemplary embodiment of the invention, miniature plastic scintillating fiber detectors are used that have a unique combination of properties. Their water equivalence is maintained over a broad energy range (e.g., 0.2 to 25 MeV). Furthermore, they provide a highly sensitive medium, which enables small sensitive volumes (e.g., less than 2 $mm^3$) and high resolution, linearity to dose, dose rate independence, energy-independent response, and real-time readout.

Figure 1:
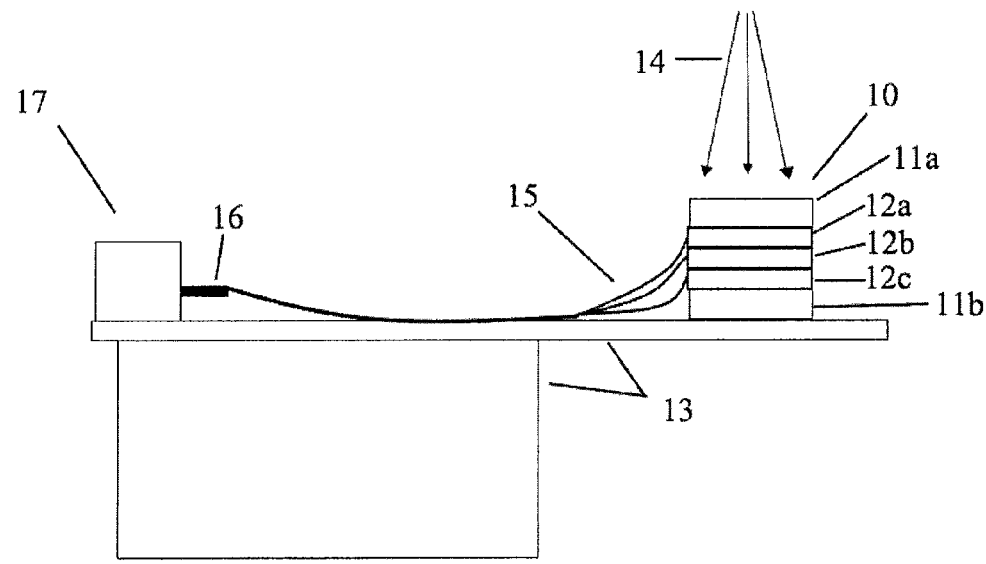
FIG. 1 is a schematic side view of a scintillating fiber dosimeter according to the present invention.

Shown in FIG. 1 is a scintillating fiber dosimeter array according to the present invention. The dosimeter is located on a radiotherapy treatment table 13, a phantom component 10 being composed of a series of water-equivalent modular slabs. Slabs 12a, 12b and 12c have scintillating fiber detectors embedded in them, while slabs 11a and 11b do not. While five slabs are shown in the embodiment of FIG. 1, those skilled in the art will recognize that it is possible to have more or fewer slabs depending on the particular application. The slabs may be made of a common plastic material with properties similar to water, such as polystyrene, acrylic or Lucite, or may be some other special chemical compound designed to be similar to water or human tissue. With the scintillating optical fibers being embedded in a water-equivalent phantom, beam perturbation is minimized.

During operation, the slabs are irradiated by a radiation beam 14. The impact of the radiation on the scintillating fiber detectors embedded in the slabs 12a, 12b and 12c results in the generation of scintillation light in the detector fibers in an amount proportional to the radiation dose detected. The scintillation light is transported by optical fiber cable 15 to photo-detector component 17, to which it is connected by a connector system 16 that provides reliable, reproducible coupling.

The phantom material and the scintillating fiber detectors may be arranged in any desired configuration. Since each of the detectors is small, and may act as a point detector, detection points may be selected as desired within a three-dimensional detection space. The embodiment shown in FIG. 1, for example, has three slabs within which detectors are embedded, as well as slabs on the top and on the bottom of the phantom in which there are no embedded detectors. These top and bottom slabs therefore serve only to provide equilibrium material for the phantom, while the detectors provide detection points within each of three different vertical planes. It may also be desired to use the detectors in an application that has no phantom. For example, the scintillating fiber detectors may be used during a radiotherapy treatment of a patient.

Figure 2:
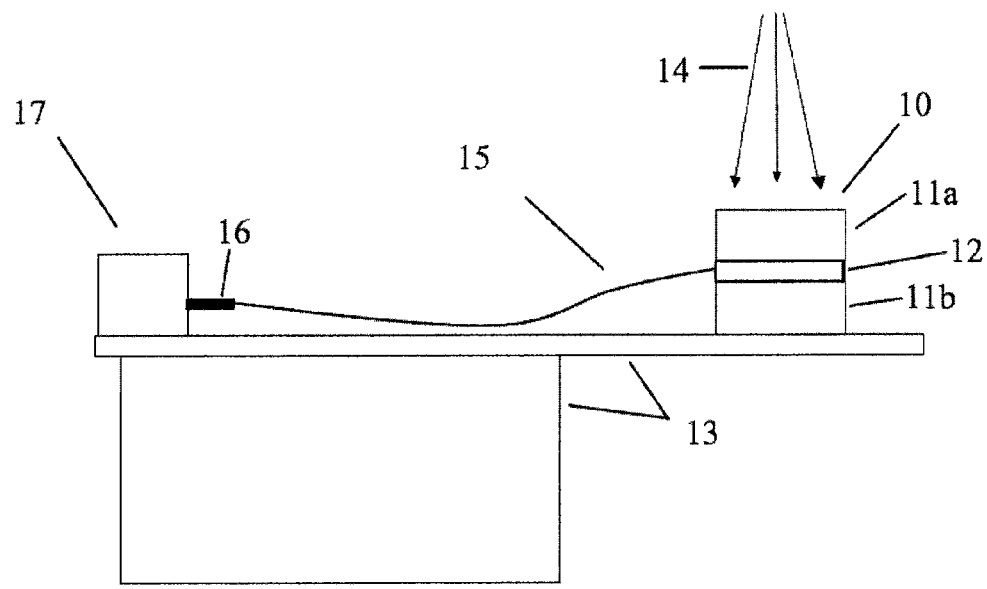
FIG. 2 is a schematic side view of a scintillating fiber dosimeter similar to that of FIG. 1, but for which a single slab is used for a phantom component.

FIG. 2 shows another example of the invention in which only a single slab 12 is used which has embedded scintillating fiber detectors. Two slabs 11a, 11b, above and below the slab 12, have no detectors, and serve only as equilibrium material. While FIGS. 1 and 2 show two possible configurations of the present invention, those skilled in the art will recognize that numerous other combinations of scintillating fiber detectors, with or without different combinations of equilibrium material, may be used without departing from the intended scope of the invention. Moreover, the slabs shown in the figures are modular, allowing them to be mixed and matched as desired to form a phantom component of a particular configuration. However, other arrangements of phantom material may also be used.

Different layouts of scintillating fibers may be used within a slab. FIG. 3A depicts one possible configuration, in which small, equal-sized pieces of the scintillating fibers are arranged in a parallel configuration, equally spaced along a midline 18 of the slab 23. The scintillating fiber segments are coupled to non-scintillating collection fibers 19, which extend from the side of the slab 23. As indicated in the figure, the scintillating fiber segments 28 occupy only a small space relative to the overall fiber combination, and the detection that they provide is therefore only along the midline 18. The lengths of combined scintillating and collection fibers may be embedded in grooves machined in the slab which, for example, may be made of water-equivalent plastic. The grooves may be of the same depth as the fiber diameter, so that the fibers are completely contained within the grooves. For example, one-millimeter diameter fibers may be embedded in grooves having a depth of one millimeter. The grooves are machined to provide a tight fit to the optical fibers, and to leave as small of an air gap as possible. As shown in the configuration of FIG. 3A, the grooves are equally spaced and extend from a first edge of the slab to the mid-line 18. The portions of the collection optical fibers that protrude from the slab 23 together form optical cable 15 that is connected to the photo-detector component 17 (as shown in FIGS. 1 and 2).

FIG. 3B shows another possible configuration for fibers embedded in a detector slab 23. In this example, the detector fibers are arranged in the shape of the letter "X," which allows them to provide more spatial information. As in the arrangement of FIG. 3A, the scintillating fiber segments of FIG. 3B are located only at the very end of the fibers shown in the figure, e.g., in the last one millimeter. In this configuration, half of the detectors are located at the ends of the collection fibers of fiber group 22, which are embedded in one side of the slab 23, one quarter of the detectors are located at the ends of the collection fibers of fiber group 20, which are embedded in a direction perpendicular to the group 22, and the remaining one quarter of the detectors are located at the ends of collection fibers of fiber group 21, which extend from the side of the slab 23 opposite that of group 20. Thus, the scintillating fiber detectors, being very short, together form an "X" shape across the slab 23, and thereby represent a variety of detection points spanning a two-dimensional space.

Figure 3C:
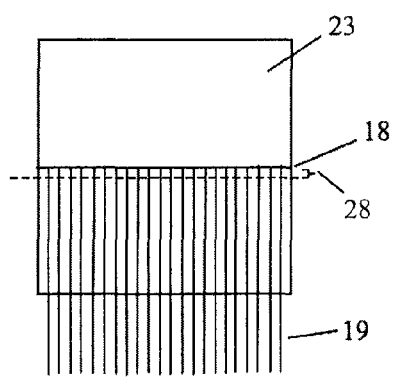
FIG. 3C is a cross sectional view of a water-equivalent slab according to the present invention having scintillating fiber detectors fully embedded inside.
Figure 3C:
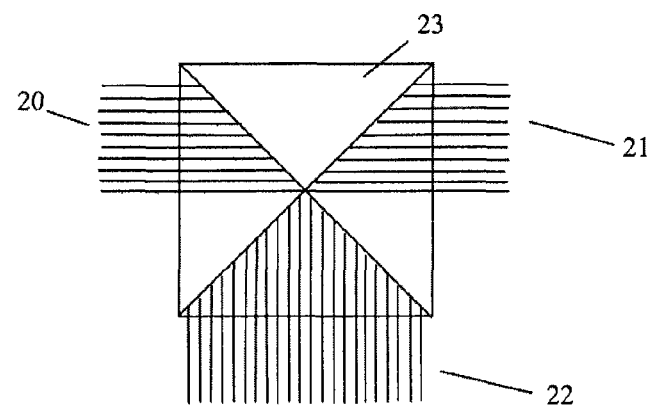
Figure 3C:
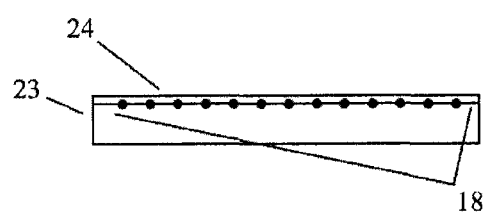

For a slab within which fibers are embedded in grooves made in the slab, it may be desirable to fix a thinner slab of water-equivalent material with shallow grooves atop the slab holding the fiber detectors. FIG. 3C is a schematic view showing a cross section of two such slabs 23, 24 that are fixed together, for example, by glue to form what is essentially a single slab. This configuration allows the fiber detectors to be tightly surrounded by equilibrium material, with little or no air space in between. It may also serve to keep a light-tight enclosure around the scintillating fiber detectors, so that no external light can reach them.

Figure 4:
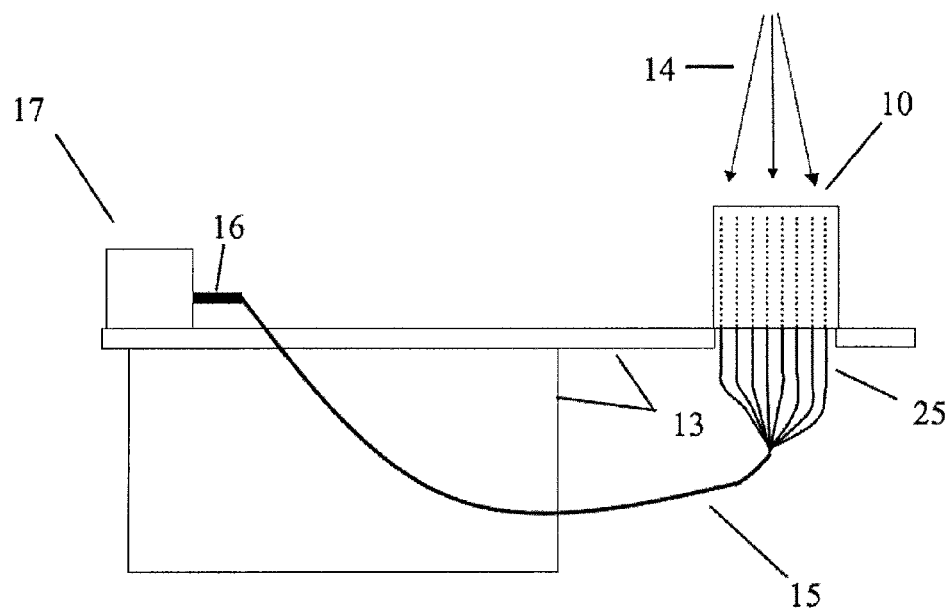
FIG. 4 is a schematic view of an embodiment of the invention in which the scintillating fiber detectors are embedded in a vertical direction in a water-equivalent slab.

Another embodiment of the invention is shown in FIG. 4. In this embodiment, the fiber detectors are oriented in a vertical configuration, such that the terminal ends of the fibers face toward the radiation source. That is, rather than the fibers being oriented in a direction perpendicular to a transmission direction of the radiation source, they are parallel thereto. This configuration allows the scintillating fiber detector to have a smaller cross section relative to the beam direction and therefore better spatial resolution. As in the other orientations, the scintillating fiber segments are relatively short, and are coupled to collection fibers 25 that protrude from the bottom of the slab and together form the optical cable 15 that is connected to coupler 16. The scintillating fiber segments may each be located as desired within the three-dimensional space of the phantom material 10, thus allowing a user to tailor the detection arrangement to a specific application.

The configurations shown in FIGS. 3A-3C and 4 show only a small number of detectors shown to provide for better clarity. However, those skilled in the art will understand that many more detectors may be used to provide good resolution within the detection space.

Figure 5A:
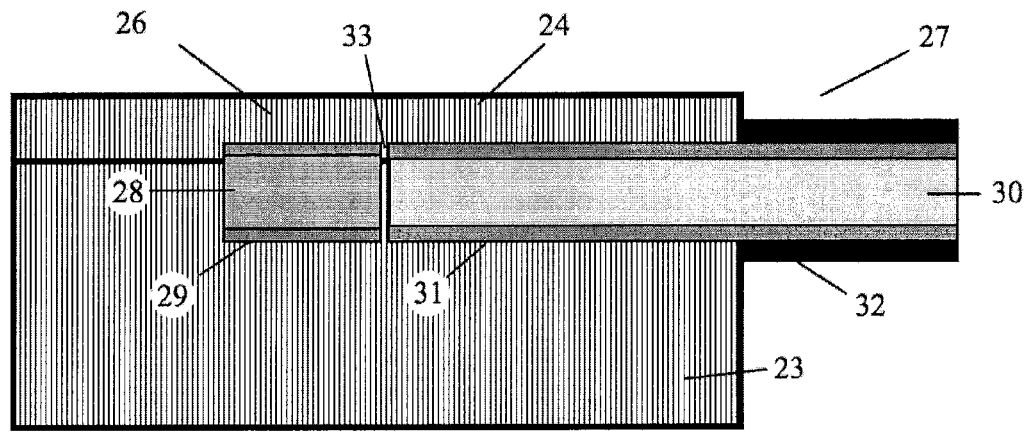
FIG. 5A is a detailed schematic view of a scintillating fiber detector that may be used with the present invention.

FIG. 5A is detailed schematic view of a scintillating fiber as it might be embedded in the slabs of a phantom component of the present invention. A piece of scintillating fiber 26 is coupled to a light carrying optical collection fiber 27. The scintillating fiber 26 has a core 28 that produces scintillation if stimulated by radiation, and a non-scintillating cladding 29 that improves the guidance of scintillation light produced in the core 28. The collection fiber 27 also possesses a core 30 and cladding 31 but does not produce scintillation. A black jacket 32 surrounds the portion of the collection fiber 27 that is external to the water-equivalent slab to shield it from ambient light. A coupling 33 between the scintillating fiber 26 and the light carrying optical fiber 27 is made with a bonding agent that will minimize the differences in refractive index between the scintillating fiber 26 and the light carrying optical fiber 27. A lens, a fiber optic taper or other device may also be inserted in the coupling region to increase coupling efficiency.

Figure 5B:
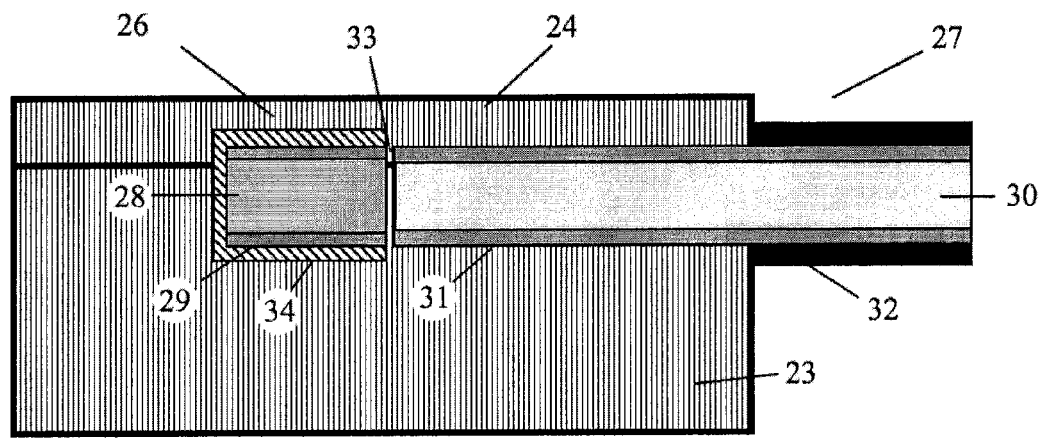
FIG. 5B is a detailed schematic view of a scintillating fiber detector similar to that of FIG. 5A, but for which the detector is coated with a reflective material.

The embodiment shown in FIG. 5B is similar to that of FIG. 5A, but a reflective coating is added to the scintillating fiber. The reflective coating surrounds the piece of scintillating fiber, except for the portion that is coupled to the non-scintillating fiber 27. The use of this reflective coating tends to increase the collection of a usable amount of light by the scintillating fibers in that it minimizes loss from the fiber by reflecting inward scintillation light generated therein. The reflective coating may also act as a shield by preventing external light from entering the fiber segment. In this way, the entry of ambient light into the fiber is minimized.

Figure 6A:
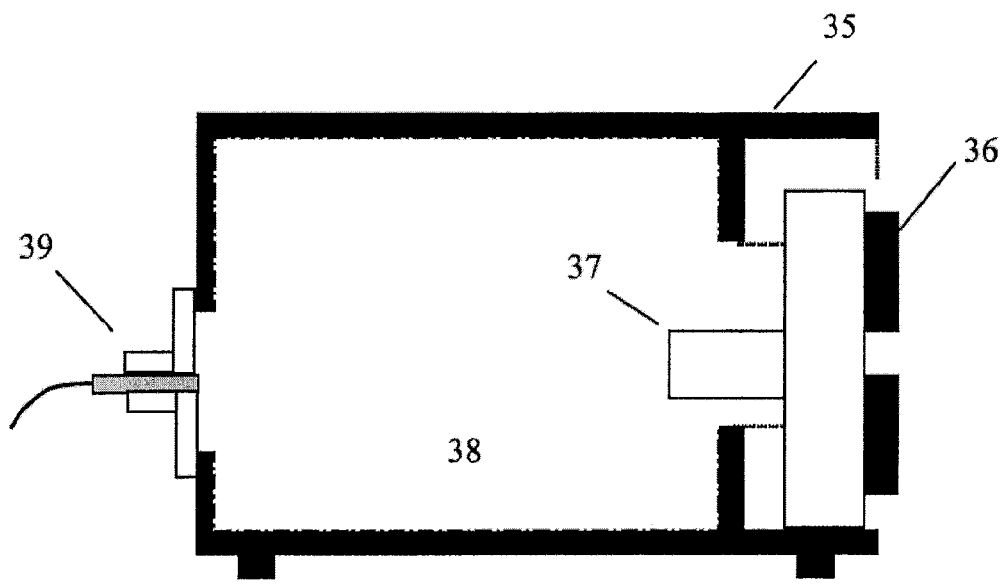
FIG. 6A is a schematic view of a photo-detector component that may be used with the present invention.

A photo-detector system that may be used with the scintillating fiber detector of the present invention is shown in FIG. 6A. An external casing 35 anchors the photo-detector components, and shields them from ambient light. An imager 36 converts the light coming from the input fiber optic cables to a quantitative electronic signal in the form of an image. The imager can be a CCD camera, a CMOS sensor, or any other device capable of producing a reproducible image either in monochrome or color with the level of light produced by the scintillating fiber detectors. Also located within the external casing are an objective lens 37, an intermediate space 38 and a connector system 39, which connects the non-scintillating optical fiber to the photo-detector system. The outer casing may be made of thick metal to act as a radiation shield that will protect the imager 36 from stray radiation. In case where the thickness is not sufficient to completely protect the imager, a post-processing algorithm may be used to remove transient noise produced by scatter radiation.

Figure 6B:
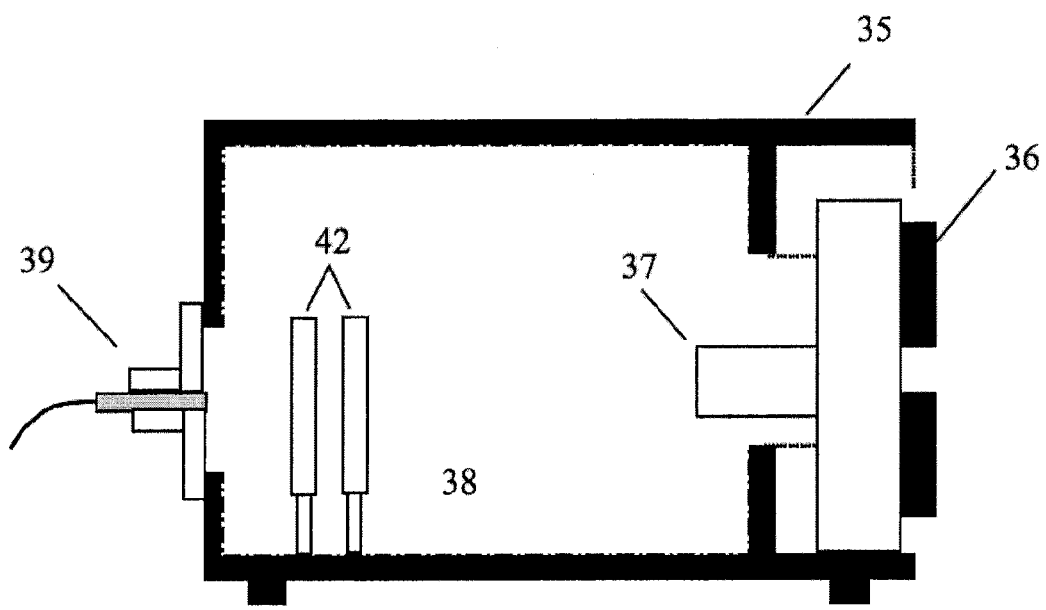
FIG. 6B is a schematic view of a photo-detector component similar to that of FIG. 6A, and which includes a set of optical filters and mirrors.

A variation of the photo-detector system of FIG. 6A is shown in FIG. 6B. In this embodiment, a set 42 of optical filters and mirrors is added to the intermediate space 38 to allow for filtration or separation of undesired light from another source such as Cerenkov radiation. Such an undesired light source can contribute to the noise of the system, and it is desirable to remove it. Filtration can be achieved by different techniques including, but not limited to, the use of band-pass filters to isolate the spectral component of the scintillation emission spectrum that overlaps only minimally with that of the undesired light source. One other possible way of filtering the undesired light source is by measuring the signal that contains both the scintillation light and the overlapping undesired light with different color filters, thereby applying spectral decoupling.

The objective lens 37 of the photo-detector system collects the light from the optical fiber coupled to the connector system 39 and projects an image onto the photosensitive surface of the imager 36. This allows for simultaneous reading of the output of all the scintillation detectors coupled to the connector system. For maximal collection efficiency, this objective lens should have a small F-number. The collection fibers are coupled to the connector system in a known arrangement, such that a correlation is made between the signal detected from each fiber and the corresponding scintillating fiber detector within the detection space. Thus, the image projected onto the imager is indicative of the distribution of radiation for the detectors that are coupled to the connector system 39. Those skilled in the art will recognize that the specific correlation between the image of the photo-detector system and the spatial location of the detectors is completely customizable, and may be selected as desired by the user.

Figure 7:
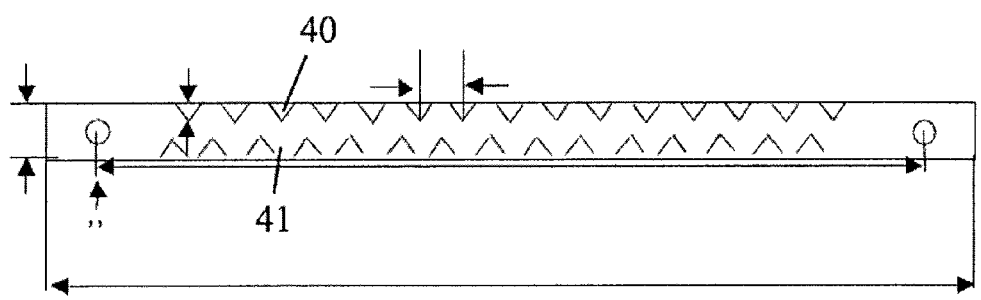
FIG. 7 is a cross sectional view of a connector system that may be used with a scintillating fiber dosimeter array according to the present invention.

Mechanical reproducibility is an important feature of an absolute dosimeter array. Shown in FIG. 7 is a schematic view of a connector system that may be used with the present invention. The connector attaches to the photo-detector system and is configured so as to accommodate a plurality of non-scintillating collection fibers that transport light from the fiber detectors. The connector shown in FIG. 7 has a plate with a row of grooves 40 within which the collection fibers reside. The grooves are spaced at an equal pitch (e.g., two millimeters) along the length of the connector, and may thereby serve to fix numerous fibers in an equally-spaced configuration. The grooves may be sized so that each provides just enough space for one of the collection fibers. Thus, if a flat surface is placed atop the plate portion containing the grooves, the fibers are snugly contained within the groove space, with very little air space surrounding them. This helps to minimize noise from being introduced due to stray ambient light. It also provides for the ability to stack several plates together to form a connector with multiple rows of collection fibers. The plate having the grooves 40 in FIG. 7 also has a second set of grooves 41 on the opposite side. The set of grooves 41 can accommodate another row of collection fibers in the same manner as the set of grooves 40. As this plate is stacked on another plate with a flat top surface, the fibers are snugly contained within the grooves 41.

Those skilled in the art will understand that the connector may have multiple plates with different number of grooves as may be desired by the user. Moreover, for clarity the drawing shows a relatively small number of grooves per row, and each row may have many more grooves. For example, in one embodiment, a connector may hold sixty fibers per row. In addition, several of the connectors can be mounted to the external casing of the photo-detector system thus allowing a very large number of optical fibers to be read simultaneously by the imager. By virtue of the predictable groove configuration, the connector enables repeatable positioning of the fibers relative to the imager across multiple connector insertion and extraction cycles. It is also desirable that all of the fibers being imaged simultaneously have their ends (from which optical energy is emitted) in a common plane. This allows for proper imaging of the optical outputs onto the image. Also shown in FIG. 7 are mounting holes 45, by which the connector may be mounted to the photo-detector system. These mounting holes aid in repeatable positioning of the connector relative to the photo-detector.

Figure 8A:
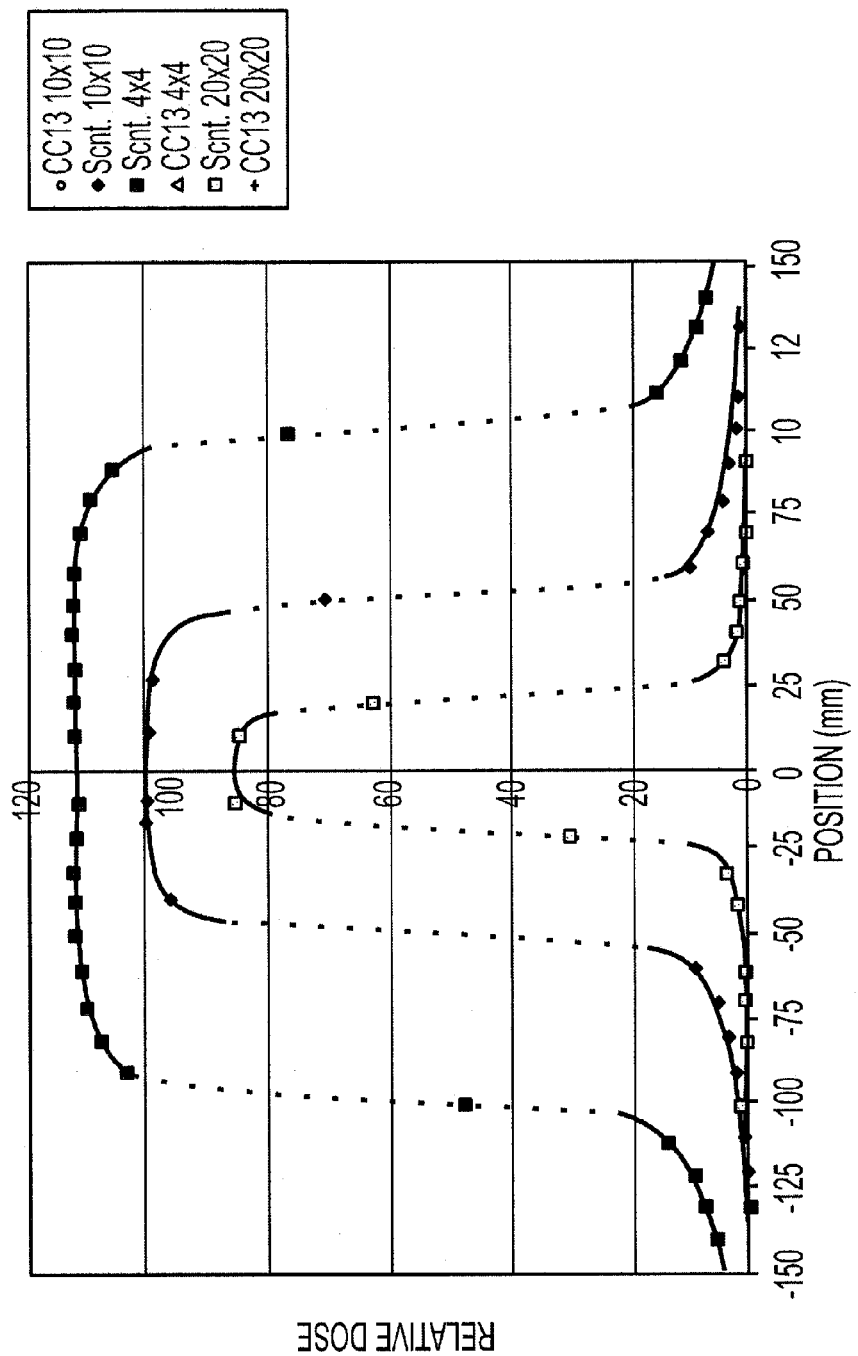
FIG. 8A is a graphical depiction of a relative radiation dose measurement taken using a scintillating fiber dosimeter array according to the present invention, for which the dose distribution of a radiotherapy beam is in a lateral direction.
Figure 8B:
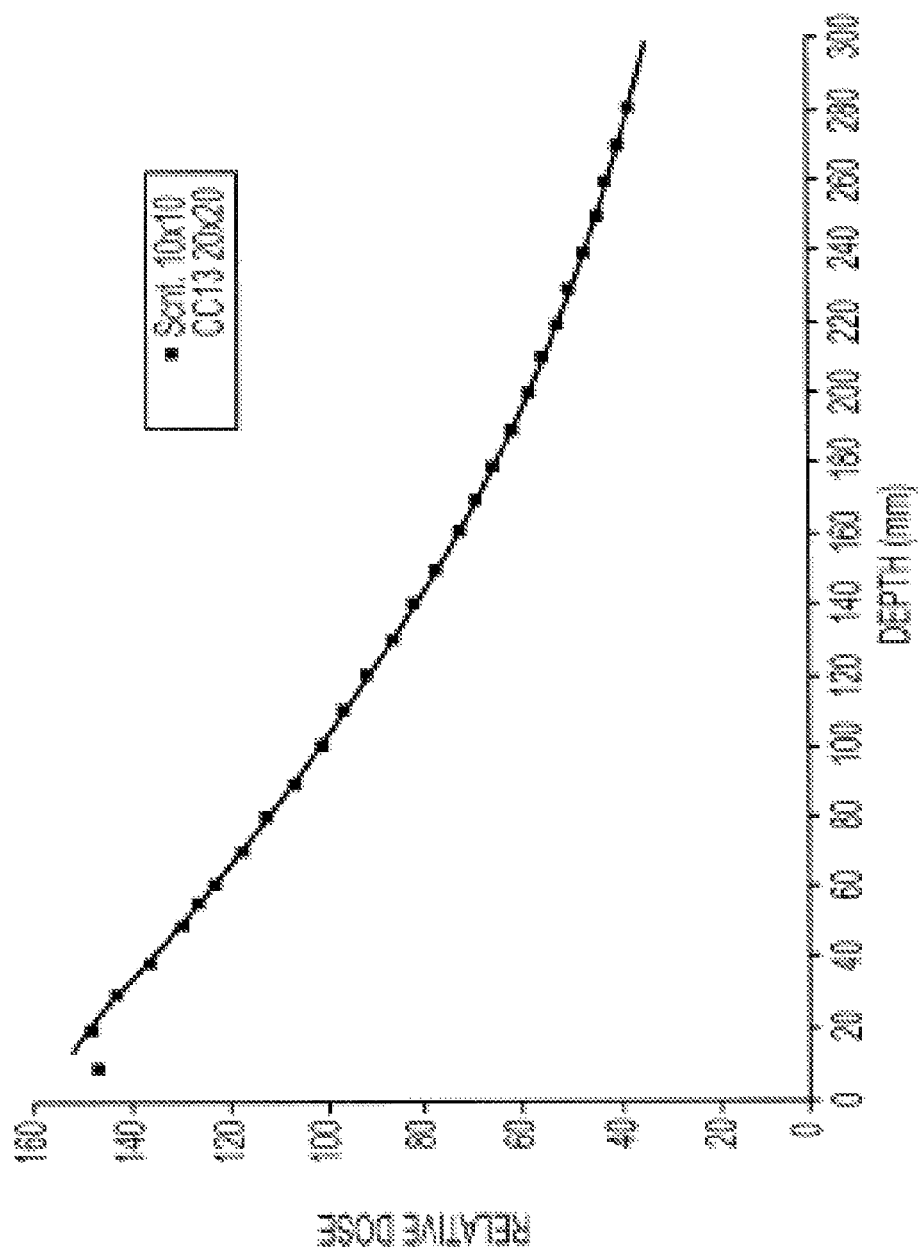
FIG. 8B is a graphical depiction of a relative radiation dose measurement taken using a scintillating fiber dosimeter array for which a dose distribution of a radiotherapy beam is in an axial direction.

FIGS. 8A and 8B are graphical depictions of dosimetry measurements obtained with a scintillating fiber dosimeter array such as that shown in FIG. 2, using a slab containing scintillating fiber detectors 12 in a configuration like that depicted in FIG. 3A. For this specific application, twenty-nine detectors were embedded in the slab 12. FIG. 8A shows the results of measurement of three different "in-plane" beam profiles. The respective field sizes (i.e., the collimated beam sizes at a distance of 100 cm from the source) for the three results shown in the figure are 4×4, 10×10 and 20×20, all in square centimeters. The corresponding results in FIG. 8A (having a position axis in millimeter units) are based on a standard calibration using a conventional calibration method, and suffer from some inaccuracies in the tail (out-of-field) of the distributions.

FIG. 8B shows a depth-dose curve acquired with the same apparatus as is used for the results shown in FIG. 8A. In each of FIG. 8A and FIG. 8B, the symbols making up the points on the curves represent measurements performed with the present invention, while the lines represent measurements taken with a single ion chamber scanned across a volume of water. Thus, as can be seen, the scintillating fiber detector array provided a correct relative output factor (within 0.3%) for each of the different field sizes. The standard deviation on a series of ten consecutive measurements was less than 1% within the field. The maximum relative difference between the scintillation detector and ionization chamber was equal to 0.9% in-field for the profiles (FIG. 8A) and 1.6% for the depth dose (FIG. 8B).

Also provided with the present invention is a calibration method for the dosimeter described herein. One of the issues facing the fiber dosimeter is the presence of ionizing radiation called Čerenkov radiation, which is a parasitic optical signal caused by the interaction of high energy electrons with the light-carrying optical fiber that transmits the optical signal from the scintillating fiber. The Čerenkov radiation represents optical noise with a wavelength range that overlaps with that of the optical signal from the scintillating fiber. Thus, an accurate measurement requires that the effect of the Čerenkov radiation be accounted for in determining the dose from the scintillation light.

The dose measured using a scintillating fiber dosimeter may be characterized as a linear combination of light measured in two orthogonal spectral windows. In practice, light in two different spectral windows may be measured from a light signal in a collection fiber by using a detector capable of discriminating the different wavelength ranges or, for example, by using a photodiode with an appropriate set of filters. In the following example, two spectral ranges are considered, referred to herein as the "blue range" and the "green range." If the variable "B" is used to designate the magnitude of the blue light and "G" used to represent the magnitude of the green light, and "a" and "b" used to represent the respective calibration coefficients for these two values, the dose, "D", may be represented as:

$$D=aB+bG \quad (1)$$

While this relationship may be used to calculate dose, it is necessary to perform two calibration steps to determine the values of the two calibration coefficients "a" and "b."

The total measured light signal may also be represented as a combination of the scintillation light and the Čerenkov radiation light in each of the two spectral channels. Thus:

$$B=B^s+B^c, \text{ and}$$

$$G=G^s+G^c \quad (2)$$

where $B^s$ is the scintillation light in the blue channel, $B^c$ is the Čerenkov radiation light in the blue channel, $G^s$ is the scintillation light in the green channel and $G^c$ is the Čerenkov radiation light in the green channel. Inserting these terms into equation (1) yields:

$$D=a(B^s+B^c)+b(G^s+G^c) \quad (3)$$

In the absence of scintillation, the value of the dose must be zero, so equation (3) must respect the condition: D=0 if $B_s$=0 and $G^s$=0, so:

$$0=aB^c+bG^c,$$

which, if put in terms of the calibration coefficient for the green channel, gives:

$$b=-a(B^c/G^c) \quad (4)$$

If this expression is then inserted back into equation (1), the result is:

$$D=a[B-(B^c/G^c)G] \quad (5)$$

As discussed below, this expression may be used for determining the calibration coefficients for when the blue channel represents the spectral emission window of the scintillator, i.e., when the scintillator is a "blue" scintillator. Similarly, when the green channel represents the spectral emission window of the scintillator (i.e., for a green scintillator), the value of the gain coefficient for the blue channel "a" may be isolated to give:

$$a=-b(G^c/B^c)$$

and equation (1) rewritten as:

$$D=b[G-(G^c/B^c)B] \quad (6)$$

Figure 9A:
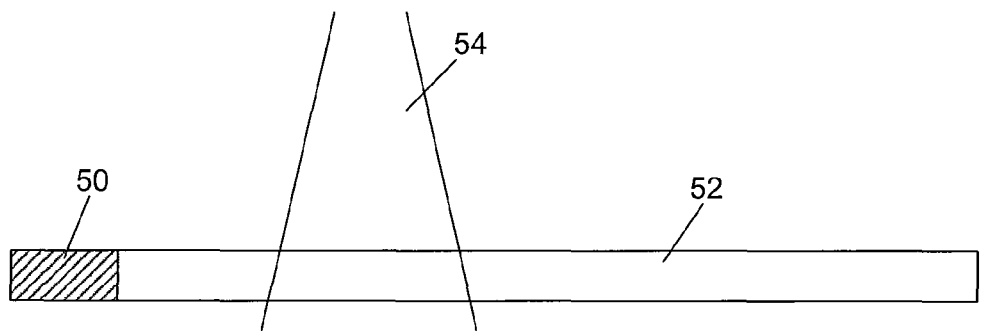
FIG. 9A is a schematic depiction of a first measurement step for a calibration procedure according to the present invention.

Equations (5) and (6) above represent alternative ways to write equation (1), and each still has two calibration coefficients. The first coefficient represents the gain factor of the detector ("a" or "b"), while the second represents the color ratio of the Čerenkov light ($B^c/G^c$ or $G^c/B^c$). Using a calibration method according to the present invention, the value of these coefficients may be determined from the system. Shown in FIG. 9A is a schematic view of a scintillating fiber segment 50 coupled to a non-scintillating collection fiber 52. A radiation beam 54 is depicted as intersecting a portion of the collection fiber 52, but not the scintillating fiber segment 50. In the exemplary embodiment, the fiber is irradiated close to the scintillator, but far enough to avoid the production of any scintillation. Thus, with this manner of irradiation, only Čerenkov radiation is produced, and no light from scintillation. The measurement of this signal allows the determination of the calibration coefficient $B^c/G^c$ or $G^c/B^c$ through the calculation of the ratio of luminosity collected in the two spectral windows (in this example, the blue and green channels).

Figure 9B:
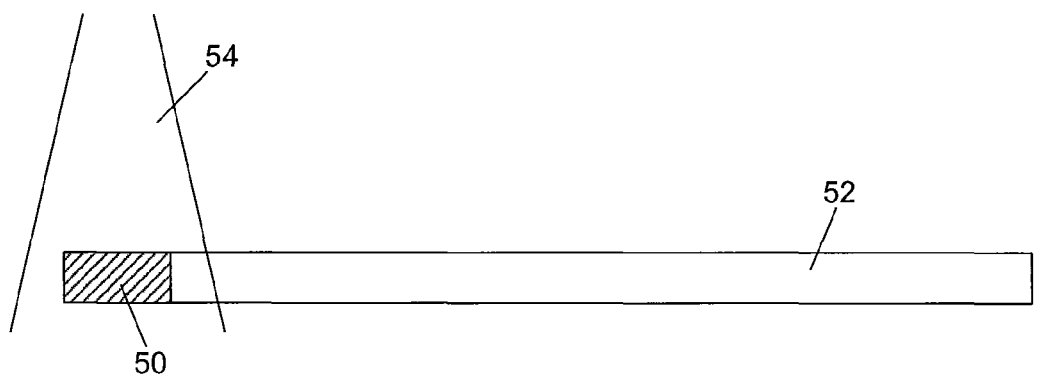
FIG. 9B is a schematic depiction of a second measurement step for a calibration procedure according to the present invention.

A second measurement, shown in FIG. 9B, involves the location of the scintillating fiber segment 50 at a point of known dose D. The measurement of this signal thereby allows the determination of the gain coefficient "a" or "b" of the dosimeter. In this embodiment, scintillation light must be produced, although the size and characteristics of the radiation field are otherwise not important. It is not necessary to produce Čerenkov radiation, although doing so will not significantly alter the measurement process. From equations (5) and (6) shown above, the value of the calibration coefficient ($B^c/G^c$ or $G^c/B^c$, respectively) is known for the spectral window in question. This acquired value may therefore be substituted into the appropriate one of equation (5) or (6), leaving the gain coefficient as the only unknown. For a blue scintillator, the value of the calibration coefficient $B^c/G^c$ may be determined from the first measurement, and that value used to solve for the gain coefficient "a" in equation (5), thereby yielding:

$$a = \frac{D}{\left[B2 - \left(\frac{B^c}{G^c}\right) * G2\right]}$$

where B2 and G2 are the luminosities measured during the second measurement in the blue and green channels, respectively. Since the dose value, D, is known, and the value of the calibration coefficient $B^c/G^c$ is determined from the first measurement, the gain coefficient "a" can be determined. The same process may be used for the case of a green scintillator, such that the gain coefficient "b" may be determined using the relation:

$$b = \frac{D}{\left[G2 - \left(\frac{G^c}{B^c}\right) * B2\right]}$$

where B2 and G2 are the luminosities measured during the second measurement in the blue and green channels, respectively, D is the known dose value and the value of the calibration coefficient $G^c/B^c$ is determined from the first measurement.

Those skilled in the art will understand that the method described above is not specific to "blue" or "green" channels, and that it may be thought of more generically in terms of two optical wavelength spectral windows. A first spectral window should fit the emission spectrum of the scintillator used. In general, a scintillator may be described as having a known emission spectrum $S(\lambda)$, where $\lambda$ is optical wavelength. A second spectral window may then be defined as the integral of this emission spectrum plus the Čerenkov emission spectrum $C(\lambda)$ in the second spectral window (delimited by the wavelengths $\lambda 1$ and $\lambda 2$). The luminosity in the second channel may therefore be represented by:

$$L = \int_{\lambda 1}^{\lambda 2} (S(\lambda) + C(\lambda)) d\lambda$$

Moreover, while the calibration method is described with reference to a single scintillator/collection fiber combination, those skilled in the art will recognize that the process may be applied to a system having any number of scintillator/fiber elements. In addition, when using fiber components having the same material and construction, and the same signal optical detection for each of the scintillator/collection fibers of the system, the calibration of one scintillator/collection fiber may be applied to the others of the system.

Figure 10:
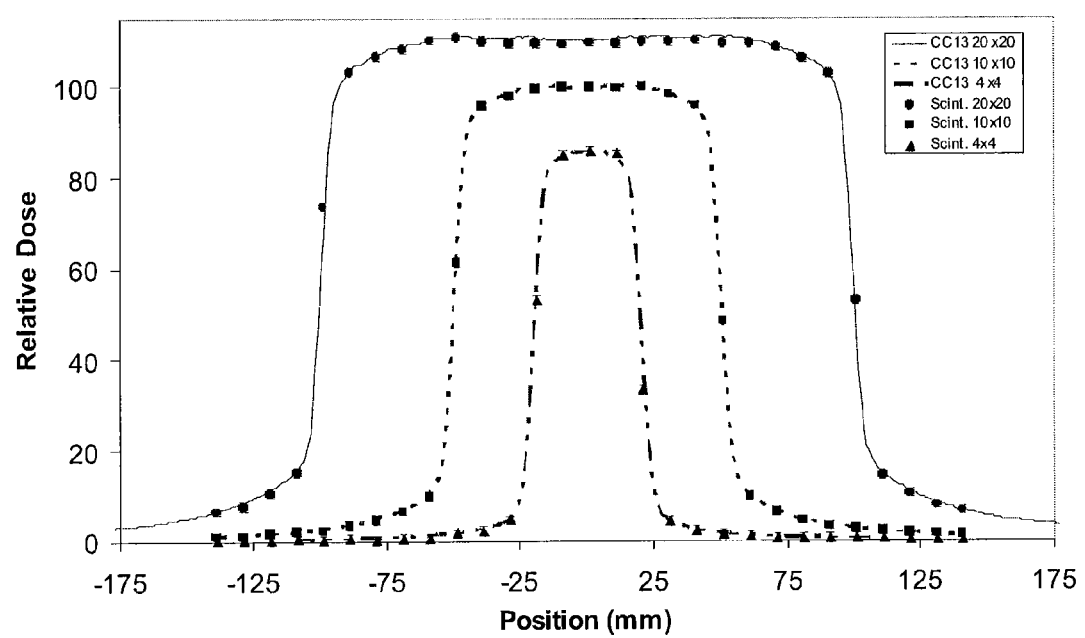
FIG. 10 is a graphical depiction of a relative radiation dose measurement similar to that shown in FIG. 8A, but which made use of a more accurate calibration method according to the present invention.

An earlier proposed calibration method using a subtraction of the Čerenkov contribution relied on the assumption that the attenuation of the optical fiber was the same in the two channels. However, while being a reasonable approximation, this is not true, and the result was errors in the extraction of the calibration coefficients. In the method of the present invention, two very extreme conditions are used to extract the calibration factors. This results in robust parameters that can be used in any clinical configurations. Since $B^c/G^c$ (or $G^c/B^c$) has to be measured only once for a given fiber, this reduces the number of steps necessary for performing a calibration, and better agrees with certain calibration protocols, which are often formulated in term of one specific point of dose. The method also simplifies the calibration protocol for certain brachytherapy and radiosurgery applications as it eliminates the influence of the radiation field dimension. As mentioned above, in the measurement shown in FIG. 9A, the size of the radiation field is of no importance and, in the second measurement shown in FIG. 9B, it is only important to provide a dose at the scintillator in order to produce scintillation light. Removing the need to control field dimension for calibration is highly beneficial to brachytherapy and radiosurgery applications, which can produce only a small field size (typically less than a five centimeter diameter). As an example of the improved accuracy using the calibration method described above, FIG. 10 shows the same in-plane beam profiles as are depicted in FIG. 8A. These profiles were measured using the same scintillation fiber detectors in the same conditions as in FIG. 8A, but made use of the new calibration method.

The present invention enables rapid and accurate measurements of the most complex radiation therapy treatment modalities such as IMRT, tomotherapy and radiosurgery. Due to the unique properties of the plastic scintillating fiber, the total time required for mandatory quality assurance tests of these complex treatment modalities is minimized. The dosimeter described herein possesses the accuracy and precision of a single point detector without requiring time-consuming processing such as the development or scanning of films. The scintillating fiber detectors of the invention are also fully water equivalent so as to not cause perturbation of the beam even when the detectors are closely distributed in three-dimensional space.

While the invention has been shown and described with reference to a preferred embodiment thereof, it will be understood by those skilled in the art that various changes in form and detail may be made herein without departing from the spirit and scope of the invention as defined by the appended claims.

What is claimed is:

1. A radiation dosimeter for measuring a relative dose of a predetermined radiation type within a detection region, the dosimeter comprising:
    a plurality of scintillating optical fibers located within the detection region that generate optical energy in response to irradiation with said predetermined radiation type;
    a plurality of collection optical fibers optically coupled to the scintillating optical fibers such that optical energy generated by the scintillating optical fibers is coupled into the collection optical fibers and transmitted thereby;
    a photo-detector to which the collection optical fibers are coupled, the photo-detector generating electrical signals indicative of optical energy transmitted by the collection optical fibers; and
    a phantom material within which at least one of the scintillating fibers is embedded, the phantom material comprising a plurality of modular slabs, the plurality of modular slabs including scintillating fibers therein on at least two different vertical planes.

2. A radiation dosimeter according to claim 1 wherein the phantom material comprises a water-equivalent material.

3. A radiation dosimeter according to claim 1 wherein at least one of the modular slabs has no scintillating optical fiber embedded therein.

4. A radiation dosimeter according to claim 1 wherein the scintillating fibers are located in the detection region such that a longitudinal axis of each scintillating fiber is perpendicular to a transmission axis of a beam of said predetermined radiation type.

5. A radiation dosimeter according to claim 4 wherein the scintillating fibers are substantially all parallel to one another.

6. A radiation dosimeter according to claim 4 wherein the scintillating fibers reside in a plurality of planes, each of which is perpendicular to the radiation transmission axis.

7. A radiation dosimeter according to claim 1 wherein the scintillating fibers comprise at least some scintillating fibers that are oriented such that a longitudinal axis of each thereof is parallel to a transmission axis of a beam of said predetermined radiation type.

8. A radiation dosimeter according to claim 1 further comprising a connector that provides optical coupling between the transmission optical fibers and the photo-detector.

9. A radiation dosimeter according to claim 8 wherein the connector maintains output ends of the transmission optical fibers that are coupled to the photo-detector so that they are equally spaced along an optical input to the photo-detector.

10. A radiation dosimeter according to claim 1 wherein the scintillating optical fibers comprise scintillating optical fibers each of which has a reflective coating surrounding it so as to maintain internal reflection of light within the fiber.

11. The radiation dosimeter of claim 1, wherein at least one of modular slabs includes a thinner slab portion affixed to a thicker slab portion with the at least one of the scintillating fibers secured in a groove between the thinner slab portion and the thicker slab portion so as to provide a light-tight enclosure around the scintillating fiber detector.

12. A radiation dosimeter for measuring a relative dose of a predetermined radiation type within a detection region, the dosimeter comprising:
   a phantom material located in the detection region;
   a plurality of scintillating optical fibers embedded in the phantom material that generate optical energy in response to irradiation with said predetermined radiation type;
   a plurality of collection optical fibers each optically coupled to at least one of said scintillating optical fibers such that optical energy generated by one of the scintillating optical fibers is coupled into a collection optical fiber and transmitted thereby;
   a photo-detector that receives optical energy from the collection optical fibers and generates electrical signals indicative of optical energy transmitted by the collection optical fibers; and
   a connector that maintains output ends of the collection optical fibers in a predetermined spatial relationship relative to one another and provides repeatable optical coupling of the collection optical fibers to the photo-detector,
   wherein the phantom material comprises a plurality of modular slabs, the plurality of modular slabs including scintillating fibers therein on at least two different vertical planes.

13. A radiation dosimetry method for measuring a relative dose of a predetermined radiation type within a detection region, the method comprising:
   locating a plurality of scintillating optical fibers within the detection region, the scintillating optical fibers generating optical energy in response to irradiation with said predetermined radiation type;
   coupling to the scintillating optical fibers a plurality of collection optical fibers such that optical energy generated by the scintillating optical fibers is coupled into the collection optical fibers and transmitted thereby; and
   detecting the optical energy transmitted by the collection optical fibers with a photo-detector which generates an electrical signal indicative of the optical energy transmitted by the collection optical fibers;
   wherein a phantom material is located within the detection region and the phantom material comprises a plurality of modular slabs, the plurality of the modular slabs having at least a portion of the scintillating optical fibers embedded therein on at least two different vertical planes.

14. A method according to claim 13 wherein a longitudinal axis of the scintillating fibers is perpendicular to a transmission axis of a beam of said predetermined radiation type.

15. A method according to claim 13 wherein a longitudinal axis of at least some of the scintillating fibers is parallel to a transmission axis of said predetermined radiation type.

16. A method according to claim 13 further comprising coupling the collection optical fibers to the photo-detector using a repeatable connector that maintains output ends of the collection optical fibers in a predetermined spatial relationship relative to one another.

17. A method of calibrating a radiation dosimeter having a scintillating optical fiber that generates optical energy in response to irradiation with a predetermined radiation type, and a collection optical fiber optically coupled to the scintillating optical fiber such that optical energy generated by the scintillating optical fiber is coupled into the collection optical fiber and transmitted thereby, wherein the dose measured by the dosimeter is proportional to a linear combination of a first dosimeter gain coefficient times the optical energy collected by the collection optical fiber in a first spectral window plus a second dosimeter gain coefficient times the optical energy collected by the collection optical fiber in a second spectral window, the first spectral window matching an emission spectrum of the scintillating optical fiber and the second spectral window being substantially outside of the first spectral window, the method comprising:
   irradiating at least a portion of the collection optical fiber with the predetermined radiation type while minimizing any irradiation of the scintillating optical fiber, and making a first measurement of the magnitude of optical energy in the collection optical fiber for each of the first spectral window and the second spectral window;
   irradiating at least a portion of the scintillating optical fiber with a known dose of the predetermined radiation type and making a second measurement of the magnitude of optical energy in the collection optical fiber in each of the first spectral window and the second spectral window;
   determining a non-scintillation optical energy ratio between the magnitude of the first measurement optical energy of the first spectral window and the magnitude of the first measurement optical energy of the second spectral window; and
   determining the first gain coefficient by dividing the known dose by a value equal to the magnitude of the second measurement optical energy in the first spectral window minus a multiplication product of the non-scintillation optical energy ratio and the magnitude of the second measurement optical energy in the second spectral window;
   wherein a phantom material is located within the detection region and the phantom material comprises a plurality of modular slabs, the plurality of the modular slabs having at least a portion of the scintillating optical fibers embedded therein on at least two different vertical planes.

18. A method according to claim 17 wherein the second spectral window comprises optical energy in a wavelength range that includes Čerenkov light resulting from irradiation of the collection fiber with the predetermined radiation type.

19. A method according to claim 17 wherein the radiation dosimeter comprises a plurality of pairs of scintillating optical fibers and accompanying collection optical fibers each being of similar construction, and wherein Čerenkov calibration values determined for one of the collection optical fibers is applied to each of the other collection optical fibers, which are subsequently calibrated for a gain coefficient.

20. A method according to claim 17 wherein the method requires only one predetermined dose measurement to determine an overall gain coefficient.

21. A radiation dosimeter for measuring a relative dose of a predetermined radiation type within a detection region, the dosimeter comprising:
   a plurality of scintillating optical fibers located within the detection region that generate optical energy in response to irradiation with said predetermined radiation type;
   a plurality of collection optical fibers optically coupled to the scintillating optical fibers such that optical energy generated by the scintillating optical fibers is coupled into the collection optical fibers and transmitted thereby;

a photo-detector to which the collection optical fibers are coupled, the photo-detector generating electrical signals indicative of optical energy transmitted by the collection optical fibers; and a phantom material having at least one light-tight enclosure within which at least one of the scintillating fibers is embedded, the phantom material comprising a plurality of modular slabs, the plurality of modular slabs including scintillating fibers therein on at least two different vertical planes.

* * * * *